United States Patent
Benderdour et al.

(10) Patent No.: US 12,398,122 B2
(45) Date of Patent: Aug. 26, 2025

(54) RESOLVIN ANALOGS COMPOUNDS, METHODS AND USES THEREOF

(71) Applicants: VALORISATION RECHERCHE HSCM, LIMITED PARTNERSHIP, Québec (CA); Julio Fernandes, Montréal (CA); Mohamed Benderdour, Pierrefonds (CA)

(72) Inventors: Mohamed Benderdour, Pierrefonds (CA); Julio Fernandes, Montréal (CA); René Maltais, Québec (CA); Jean-Yves Sancéau, Québec (CA)

(73) Assignee: VALORISATION RECHERCHE HSCM LIMITED PARTNERSHIP, Québec (CA)

( * ) Notice: Subject to any disclaimer, the term of this patent is extended or adjusted under 35 U.S.C. 154(b) by 0 days.

(21) Appl. No.: 18/730,722

(22) PCT Filed: Jan. 20, 2023

(86) PCT No.: PCT/CA2023/050065
§ 371 (c)(1),
(2) Date: Jul. 19, 2024

(87) PCT Pub. No.: WO2023/137554
PCT Pub. Date: Jul. 27, 2023

(65) Prior Publication Data
US 2025/0115588 A1 Apr. 10, 2025

Related U.S. Application Data

(60) Provisional application No. 63/301,450, filed on Jan. 20, 2022.

(51) Int. Cl.
*C07D 405/06* (2006.01)
*C07D 233/64* (2006.01)

(52) U.S. Cl.
CPC ......... *C07D 405/06* (2013.01); *C07D 233/64* (2013.01)

(58) Field of Classification Search
CPC .............................. C07D 405/06; C07D 233/64
See application file for complete search history.

(56) References Cited

FOREIGN PATENT DOCUMENTS

| CA | 1167454 | 5/1984 |
|----|---------|--------|
| CA | 2495260 | 2/2004 |
| CA | 2594310 | 7/2006 |
| CA | 2650607 | 11/2007 |

OTHER PUBLICATIONS

Koronatov, 2020, Org Lett, vol. 22, 7958-7963. (Year: 2020).*
Benabdoune et al., "The role of resolvin D1 in the regulation of inflammatory and catabolic mediators in osteoarthritis", Inflamm. Res. (Apr. 7, 2016) 65:635-645.
Benabdoun et al., "In vitro and in vivo assessment of the proresolutive and antiresorptive actions of resolvin D1: relevance to arthritis", Arthritis Research & Therapy (Mar. 12, 2019) 21:72.
De Gaetano et al., "Asymmetric synthesis and biological evaluation of imidazole- and oxazole-containing synthetic lipoxin A4 mimetics (sLXms)", European Journal of Medicine Chemistry 162 (2019) 80-108. (The year of publication is sufficiently earlier than the effective U.S. filing date so that the particular month of publication is not an issue).
Escudero-Casao et al., "Fluorinated triazole-containing sphingosine analogues. Syntheses and in vitro evaluation as SPHK inhibitors", Org. Biomol. Chem., Sep. 18, 2018, 16, 7230.
Gharpure et al., "Regioselective Synthesis of Halotriazole and their Utility in Metal Catalyzed Coupling Reactions", Eur. J. Org. Chem., Jul. 14, 2020, 6870-6886.
Koronatov et al., "Synthesis of 3-Alkoxy-4-Pyrrolin-2-ones via Rhodium(II)-Catalyzed Denitrogenative Transannulation of 1H-1,2,3-Triazoles with Diazo Esters", Org. Lett., Oct. 7, 2020, 22, 7958-7963.
Maltais et al., "A Concise, Gram-Scale Total Synthesis of Protectin DX and Related Labeled Versions via a Key Stereoselective Reduction of Enediyne", J. Org. Chem., May 12, 2023. 7088-7095.
Tungen et al., "Resolving Inflammation: Synthesis, Configurational Assignment, and Biological Evaluations of RvD1n-3DPA", Chem. Eur. J. 2019, 25, 1476-1480. (The year of publication is sufficiently earlier than the effective U.S. filing date so that the particular month of publication is not an issue).

* cited by examiner

*Primary Examiner* — D Margaret M Seaman
(74) *Attorney, Agent, or Firm* — SMART & BIGGAR LP

(57) ABSTRACT

The present application relates to resolvin analogs having anti-inflammatory and antioxidant properties, uses and methods using the same. More specifically, the present application relates to compounds of formula (I)

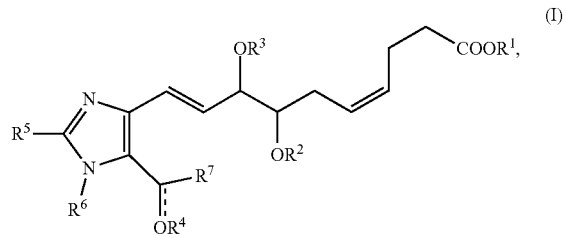

or an enantiomer, isomer, salt or solvate thereof.

26 Claims, 8 Drawing Sheets

RESOLVIN ANALOGS COMPOUNDS, METHODS AND USES THEREOF

CROSS-REFERENCE TO RELATED APPLICATIONS

The present application is a 35 USC 371 national stage entry of PCT/CA2023/050065 filed on Jan. 20, 2023, and which claims the benefit of priority of U.S. Provisional Patent Application No. 63/301,450, which was filed on Jan. 20, 2022. These documents are hereby incorporated herein by reference in their entirety.

FIELD

The present application is in the field of anti-inflammatory and antioxidant compounds. More specifically, the present application relates to resolvin analogs having anti-inflammatory and antioxidant properties.

BACKGROUND

Resolvins are a class of compounds derived from omega-3 fatty acids, primarily eicosapentaenoic acid (EPA) and docosahexaenoic acid (DHA), as well as docosapentaenoic acid (DPA) and clupanodonic acid. Resolvins belong to a class of polyunsaturated fatty acid (PUFA) metabolites termed specialized proresolving mediators (SPMs), and are classified based on the straight chain PUFA from which they are formed and/or a unique aspect of their structure. Subclasses of resolvins include resolvin Ds, resolving Es and resolvin Ts.

One of these compounds, resolvin D1 (RvD1) has been studied and shown remarkable properties in resolving inflammation, promoting tissue repair, preserving tissue integrity, treatment of bone and cartilage disorders, and the like.

However, similar to the majority of specialized proresolving mediator (SPM) members, RvD1 (7S,8R,17S-trihydroxy-4Z,9E, 11E,13Z,15E,19Z-docosahexaenoic acid) is a chemically unstable molecule that undergoes a very fast transformation to inactive products 17-oxo-RvD1 and 8-oxo-RvD1 through the enzymatic action of eicosanoid oxidoreductase. In the recent years, a number of studies conducted in vitro and in vivo studying the biological effects of SPM have resulted in the development of a variety of analogues that were tested for their ability to restore tissue homeostasis and to inhibit inflammatory processes. Given the protective effects of RvD1 against inflammation and tissue damage, it would be desired to develop metabolically stable molecule with improved pharmacokinetic and pharmacodynamics properties to improve the mode of administration for preclinical and clinical applications.

As such, there is need to provide improved compounds with similar activities to RvD1, that would at least partially alleviate the disadvantages discussed above.

SUMMARY

It has been surprisingly shown herein that compounds of the present application provide for improved stability, pharmacokinetic and pharmacodynamics properties. Comparable compounds did not display the same properties, highlighting the surprising results obtained with the processes of the application.

Accordingly, the present application includes a compound of Formula (I):

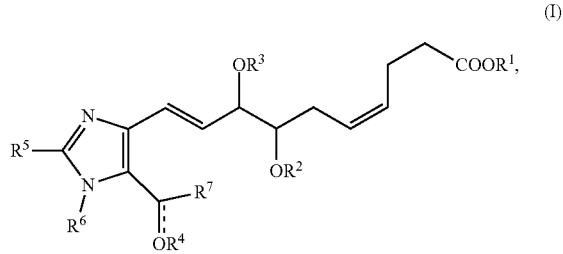

wherein
$R^1$ is selected from the group consisting of H and $C_{1-8}$ alkyl;
$R^2$, $R^3$ and $R^4$ are independently selected from the group consisting of H, $C_{1-8}$ alkyl, and a suitable protecting group; wherein $R^2$ and $R^3$ may be joined to form, together with the atom therebetween, an heterocyclyl group;
$R^5$ and $R^6$ are independently selected from the group consisting of H and $C_{1-8}$ alkyl;
$R^7$ is selected from the group consisting of linear or branched $C_{1-10}$ alkyl and linear or branched $C_{2-10}$ alkenyl, wherein the alkyl and alkenyl may be interrupted by 1 to 3 heteroatoms selected from O, N and S, and may be substituted with one or more group selected from halogen, —OH, —$CF_3$, —CN, —$NH_2$, —SH and phenyl, ╌╌ is absent or represents a bond,
wherein $R^4$ is absent when ╌╌ is a bond,
or an enantiomer, isomer, salt or solvate thereof.

The present application further includes a compound of Formula (IA):

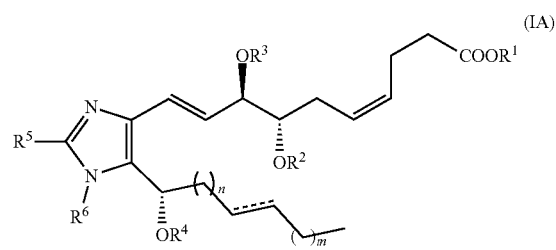

wherein $R^1$, $R^2$, $R^3$, $R^4$, $R^5$, $R^6$ and ╌╌ are as defined in claim 1, and n and m are independently an integer from 0 to 7, or an enantiomer, isomer, salt or solvate thereof.

In some embodiments, $R^7$ is pentyl, propyl, octyl or benzyl.

In some embodiments, $R^1$ is H, methyl, ethyl or propyl. In some embodiments, $R^1$ is H or methyl.

In some embodiments, $R^2$, $R^3$ and $R^4$ are independently selected from the group consisting of H, methyl, ethyl, and propyl.

In some embodiments, $R^2$ and $R^3$ are joined to form, together with the atom therebetween, an acetal group.

In some embodiments, $R^2$, $R^3$ and $R^4$ are each H.

In some embodiments, $R^5$ and $R^6$ are each H, methyl or ethyl. In some embodiments, $R^5$ and $R^6$ are each methyl.

The present application also provides a compound having the structure of Formula (I-2):

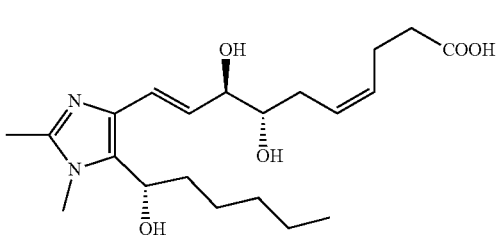

(I-2)

or an enantiomer, isomer, salt or solvate thereof.

The present application also includes a compound having the structure of Formula (I-1):

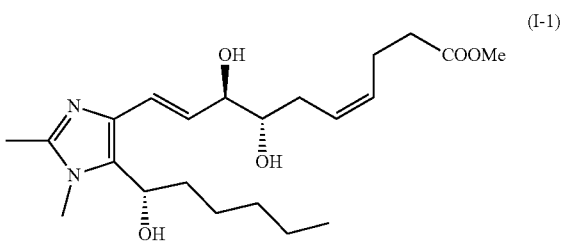 [SMILES: CCCCC[C@H](O)c1c(/C=C/[C@@H](O)[C@@H](O)C/C=C\CCC(=O)OC)nc(C)n1C]

(I-1)

or an enantiomer, isomer, salt or solvate thereof.

The present application further provides a compound having the structure of Formula (IB)

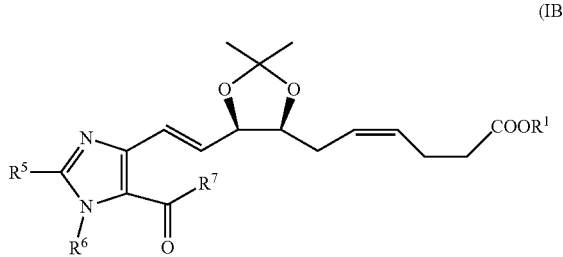

(IB)

or an enantiomer, isomer, salt or solvate thereof.

The present application also provides a compound having the structure of Formula (IC)

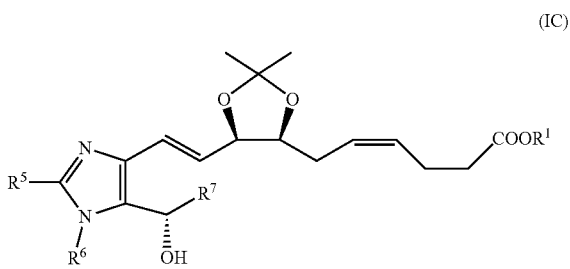

(IC)

or an enantiomer, isomer, salt or solvate thereof.

Also provided is the compound of the present application, for use in treatment or prevention of an inflammatory disease or disorder.

Also included is the compound of the present application, for use in treatment or prevention of a bone disease or disorder or joint disease and disorder.

Further provided is the compound of the present application, for use as an anti-inflammatory agent or an antioxidant agent.

Also provided is the compound of the present application, for inhibiting monocytes/macrophages differentiation.

The present application further provides a pharmaceutical composition comprising a compound of the present application, and a pharmaceutically acceptable excipient, diluent or carrier.

Also provided is the use of the compound of the present application in treatment or prevention of an inflammatory disease or disorder.

Also provided is the use of the compound of the present application, in manufacture of a medicament for treating or preventing an inflammatory disease or disorder.

Also included is the use of the compound of the present application, in treatment or prevention of a bone disease or disorder or joint disease and disorder.

Further provided is the use of the compound of the present application, in manufacture of a medicament for treating or preventing a bone disease or disorder or joint disease and disorder.

Also provided is the use of a compound of the present application, as an anti-inflammatory agent or an antioxidant agent.

Also provided is the use of a compound of the present application, for inhibiting monocytes/macrophages differentiation.

The present application further includes a method for treating or preventing an inflammatory disease or disorder, comprising administering an effective amount of a compound of the present application in a subject in need thereof.

The present application further provides a method for treating or preventing a bone disease or disorder or joint disease and disorder, comprising administering an effective amount of a compound of the present application in a subject in need thereof.

In some embodiments, the inflammatory disease or disorder is selected from arthritis, osteoarthritis, inflammatory bowel disease or disorder, and skin inflammatory disease and disorder.

In some embodiments, the bone disease or disorder is selected from osteoporosis, and bone metastases and the joint disease or disorder is arthrosis.

Further included is a method for inhibiting monocytes/macrophages differentiation, comprising administering an effective amount of a compound of the present application in a subject in need thereof; a method for inhibiting osteoclasts recruitment, comprising administering an effective amount of a compound of the present application; a method for inhibiting hyaluronic acid resorption, comprising administering an effective amount of a compound of the present application; a method for inhibiting MMP-13 production, comprising administering an effective amount of a compound of the present application; and a method for inhibiting ultraviolet-induced hyaluronic acid degradation, comprising administering an effective amount of a compound of the present application.

Also included is the use of a compound of the present application, as an antioxidant agent, a stabilizing agent or a preservative in a food composition, a cosmetic composition, a pharmaceutical composition, a petrochemical composition or a medicinal composition; use of a compound of the present application for inhibiting osteoclasts recruitment in a subject in need thereof; use of a compound of the present application for inhibiting hyaluronic acid re-sorption in a subject in need thereof; use of a compound of the present application for inhibiting MMP-13 production in a subject in need thereof; and use of a compound of the present application for inhibiting ultraviolet-induced hyaluronic acid degradation in a subject in need thereof.

Further provided is the compound of the present application, for use as an antioxidant agent, a stabilizing agent or a preservative in a food composition, a cosmetic composition, a pharmaceutical composition, a petrochemical composition or a medicinal composition.

The present application also includes a method for stabilizing or preserving a composition, comprising adding an acceptable amount of a compound of the present application as an antioxidant agent, a stabilizing agent or a preservative, wherein the composition is a food composition, a cosmetic composition, a pharmaceutical composition, a petrochemical composition or a medicinal composition.

Other features and advantages of the present application will become apparent from the following detailed description. It should be understood, however, that the detailed description and the specific examples, while indicating embodiments of the application, are given by way of illustration only and the scope of the claims should not be limited by these embodiments, but should be given the broadest interpretation consistent with the description as a whole.

BRIEF DESCRIPTION OF DRAWINGS

The embodiments of the application will now be described in greater detail with reference to the attached drawings in which.

DETAILED DESCRIPTION

1. Definitions

Figure 1:
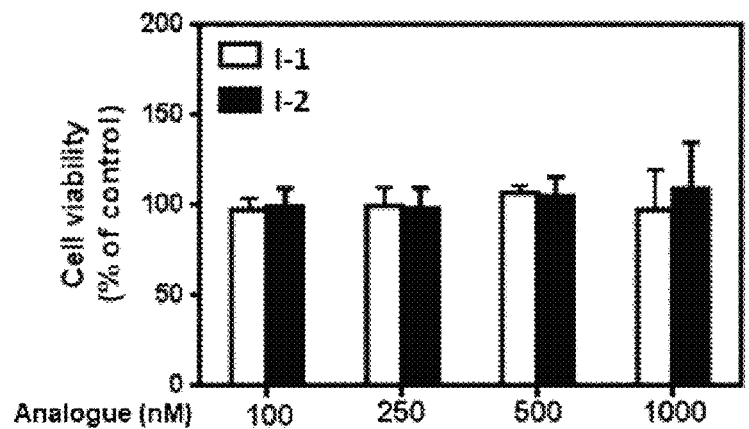
FIG. 1 shows a graph of cell viability for compounds 1-1 and 1-2 at different concentrations (0, 0,1, 0,25, 0,5, and 1 mM), according to exemplary embodiments of the present application.

Unless otherwise indicated, the definitions and embodiments described in this and other sections are intended to be applicable to all embodiments and aspects of the present application herein described for which they are suitable as would be understood by a person skilled in the art.

As used in this application and claim(s), the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

The term "consisting" and its derivatives as used herein are intended to be closed terms that specify the presence of the stated features, elements, components, groups, integers, and/or steps, and also exclude the presence of other unstated features, elements, components, groups, integers and/or steps.

The term "consisting essentially of", as used herein, is intended to specify the presence of the stated features, elements, components, groups, integers, and/or steps as well as those that do not materially affect the basic and novel characteristic(s) of these features, elements, components, groups, integers, and/or steps.

The terms "about", "substantially" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies or unless the context suggests otherwise to a person skilled in the art.

As used in the present application, the singular forms "a", "an" and "the" include plural references unless the content clearly dictates otherwise. For example, an embodiment including "a compound" should be understood to present certain aspects with one compound, or two or more additional compounds.

In embodiments comprising an "additional" or "second" component, such as an additional or second compound, the second component as used herein is chemically different from the other components or first component. A "third" component is different from the other, first, and second components, and further enumerated or "additional" components are similarly different.

The term "and/or" as used herein means that the listed items are present, or used, individually or in combination. In effect, this term means that "at least one of" or "one or more" of the listed items is used or present. The term "and/or" with respect to enantiomers, prodrugs, salts and/or solvates thereof means that the compounds of the application exist as individual enantiomers, prodrugs, salts and hydrates, as well as a combination of, for example, a salt of a solvate of a compound of the application.

The term "compound of the application" or "compound of the present application" and the like as used herein refers to a compound of Formula (I) or salts, solvates and/or enantiomers thereof.

The term "composition of the application" or "composition of the present application" and the like as used herein refers to a composition comprising one or more compounds of the application.

The term "suitable" as used herein means that the selection of the particular composition or conditions would depend on the specific steps to be performed, the identity of the components to be transformed and/or the specific use for the compositions, but the selection would be well within the skill of a person trained in the art.

The present description refers to a number of chemical terms and abbreviations used by those skilled in the art. Nevertheless, definitions of selected terms are provided for clarity and consistency.

The term "alkyl" as used herein, whether it is used alone or as part of another group, means straight or branched chain, saturated alkyl groups. The number of carbon atoms that are possible in the referenced alkyl group are indicated by the prefix "$C_{n1-n2}$". For example, the term $C_{1-10}$alkyl means an alkyl group having 1, 2, 3, 4, 5, 6, 7, 8, 9 or 10 carbon atoms.

The term "alkenyl" as used herein, whether it is used alone or as part of another group, means straight or branched chain, unsaturated alkyl groups containing at least one double bond. The number of carbon atoms that are possible in the referenced alkylene group are indicated by the prefix "$C_{n1-n2}$". For example, the term $C_{2-6}$alkenyl means an alkenyl group having 2, 3, 4, 5 or 6 carbon atoms and at least one double bond.

The term "heterocycloalkyl" as used herein, whether it is used alone or as part of another group, refers to cyclic groups containing at least one non-aromatic ring containing from 3 to 10 atoms in which one or more of the atoms are a heteroatom selected from O, S and N and the remaining atoms are C. Heterocycloalkyl groups are either saturated or unsaturated (i.e. contain one or more double bonds).

The term "aq." as used herein refers to aqueous.

The term "rt" as used herein refers to room temperature.

The term "MS" as used herein refers to mass spectrometry.

The term "LCMS" as used herein refers to liquid chromatography-mass spectrometry.

The term "NMR" as used herein refers to nuclear magnetic resonance.

The term "TLC" as used herein refers to thin-layer chromatography.

The term "DMF" as used herein refers to dimethyl formamide.

The term "Ph" as used herein refers to phenyl.

The term "Et" as used herein refers to ethyl.

The term "Ac" as used herein refers to acetate.

The term "Me" as used herein refers to methyl.

The term "Bu" as used herein refers to butyl.

The term "TSA" as used herein refers to toluenesulfonic acid.

The term "DCM" as used herein refers to dichloromethane.

The term "PPTS" as used herein refers to pyridinium p-toluenesulfonate.

The term "THF" as used herein refers to tetrahydrofuran.

The term "DMSO" as used herein refers to dimethylsulfoxide.

The term "TEA" as used herein refers to triethylamine.

The term "EDTA" as used herein refers to ethylenediaminetetraacetic acid.

The term "SEM" as used herein refers to Standard Error of the Mean.

The term "MEM" as used herein refers to Minimum Essential Medium.

The term "AMEM" as used herein refers to Alpha Minimum Essential Medium.

The term "FBS" as used herein refers to fetal bovine serum.

The term "PBS" as used herein refers to phosphate-buffered serum.

The term "RPMI" as used herein refers to Roswell Park Memorial Institute growth medium.

The term "MTS" as used herein refers to [3-(4,5-dimethylthiazol-2-yl)-5-(3-carboxymethoxyphenyl)-2-(4-sulfophenyl)-2H-tetrazolium].

The term "ANOVA" as used herein refers to analysis of variance.

The term "RANKL" as used herein refers to receptor activator of nuclear factor kappa-3 ligand.

The term "M-CSF" as used herein refers to macrophage colony-stimulating factor.

The term "TRAP" as used herein refers to tartrate-resistant acid phosphatase.

The term "TNF" as used herein refers to tumor necrosis factor.

The term "TBE" as used herein refers to Tris/Borate/EDTA buffer solution.

The term "RvD1" refers to resolvin D1, having the chemical structure:

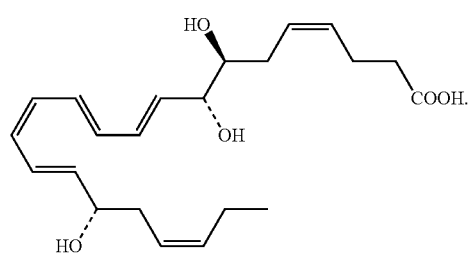 [SMILES: CC/C=C\C[C@H](O)/C=C/C=C\C=C\C=C\[C@@H](O)[C@@H](O)C/C=C\CCC(=O)O]

The term "cell" as used herein refers to a single cell or a plurality of cells and includes a cell either in a cell culture or in a subject.

The term "subject" as used herein includes all members of the animal kingdom including mammals, and suitably refers to humans. Thus the methods and uses of the present application are applicable to both human therapy and veterinary applications.

The term "pharmaceutically acceptable" means compatible with the treatment of subjects, for example humans.

The term "pharmaceutically acceptable carrier" means a non-toxic solvent, dispersant, excipient, adjuvant or other material which is mixed with the active ingredient in order to permit the formation of a pharmaceutical composition, i.e., a dosage form capable of administration to a subject.

The term "pharmaceutically acceptable salt" means either an acid addition salt or a base addition salt which is suitable for, or compatible with the treatment of subjects.

The term "solvate" as used herein means a compound, or a salt and/or prodrug of a compound, wherein molecules of a suitable solvent are incorporated in the crystal lattice. A suitable solvent is physiologically tolerable at the dosage administered.

The term "prodrug" as used herein means a compound, or salt and/or solvate of a compound, that, after administration, is converted into an active drug.

The term "treating" or "treatment" as used herein and as is well understood in the art, means an approach for obtaining beneficial or desired results, including clinical results. Beneficial or desired clinical results can include, but are not limited to alleviation or amelioration of one or more symptoms or conditions, diminishment of extent of disease, stabilized (i.e. not worsening) state of disease, preventing spread of disease, delay or slowing of disease progression, amelioration or palliation of the disease state, diminishment of the reoccurrence of disease, and remission (whether partial or total), whether detectable or undetectable. "Treating" and "treatment" can also mean prolonging survival as compared to expected survival if not receiving treatment. "Treating" and "treatment" as used herein also include prophylactic treatment. For example, a subject with early cancer can be treated to prevent progression, or alternatively a subject in remission can be treated with a compound or composition of the application to prevent recurrence. Treatment methods comprise administering to a subject a therapeutically effective amount of one or more of the compounds of the application and optionally consist of a single administration, or alternatively comprise a series of administrations.

"Palliating" a disease or disorder means that the extent and/or undesirable clinical manifestations of a disorder or a disease state are lessened and/or time course of the progression is slowed or lengthened, as compared to not treating the disorder.

The term "prevention" or "prophylaxis", or synonym thereto, as used herein refers to a reduction in the risk or probability of a patient becoming afflicted with a disease, disorder or condition.

The term "administered" as used herein means administration of a therapeutically effective amount of a compound, or one or more compounds, or a composition of the application to a cell either in cell culture or in a subject.

As used herein, the term "effective amount" or "therapeutically effective amount" means an amount of a compound, or one or more compounds, of the application that is effective, at dosages and for periods of time necessary to achieve the desired result.

II. Compounds and Compositions of the Application

It has been surprisingly shown herein that compounds of the present application provide for improved stability, pharmacokinetic and pharmacodynamics properties.

Accordingly, the present application includes a compound of Formula

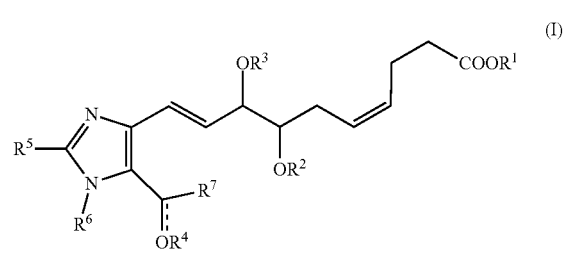

wherein $R^1$ is selected from the group consisting of H and $C_{1-8}$ alkyl;

$R^2$, $R^3$ and $R^4$ are independently selected from the group consisting of H, $C_{1-8}$ alkyl, and a suitable protecting group; wherein $R^2$ and $R^3$ may be joined to form, together with the atom therebetween, an heterocyclyl group;

$R^5$ and $R^6$ are independently selected from the group consisting of H and $C_{1-8}$ alkyl;

$R^7$ is selected from the group consisting of linear or branched $C_{1-10}$ alkyl and linear or branched $C_{2-10}$ alkenyl, wherein the alkyl may be interrupted by 1 to 3 heteroatoms selected from O, N and S, and may be substituted with one or more group selected from halogen, —OH, —CF$_3$, —CN, —NH$_2$, —SH and phenyl;

⋰ is absent or represents a bond, wherein $R^4$ is absent when ⋰ is a bond, or an enantiomer, isomer, salt or solvate thereof.

In some embodiments, $R^1$ is H, methyl, ethyl or propyl.

In some embodiments, $R^2$, $R^3$ and $R^4$ are H, methyl, ethyl or propyl or an alcohol protecting group. A skilled person would appreciate which protecting group may be used. In some embodiments, when two alcohols are on adjacent carbons, the protecting group may be joined to form, together with the atom therebetween, an heterocyclyl group. In some embodiments, $R^2$ and $R^3$ may form an acetal protecting group.

In some embodiments, $R^5$ and $R^6$ are H, methyl, ethyl or propyl.

In some embodiments, $R^7$ is linear or branched $C_{1-10}$ alkyl. In some embodiments, $R^7$ is linear or branched $C_{2-10}$ alkenyl, which may comprise 1 to 4 double bonds. In some embodiments, the $R^7$ alkyl or alkenyl chain may be interrupted by 1 to 3 heteroatoms selected from O, N and S, and may be substituted with one or more group selected from halogen, —OH, —CF$_3$, —CN, —NH$_2$, —SH and phenyl. In some embodiments, $R^7$ is pentyl, propyl, octyl or benzyl.

In some embodiments, $R^4$ is H and ⋰ represents a single bond. In some embodiments, $R^4$ is absent and ⋰ represents a double bond.

In some embodiments, the compound of Formula (I) is selected from the following:

| Compound I.D. | Structure | IUPAC Name |
|---|---|---|
| I-1 | 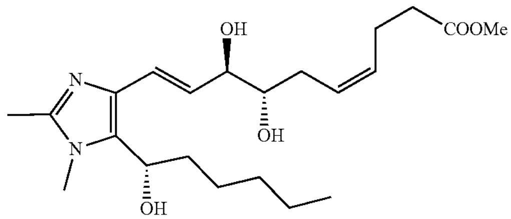 [SMILES: CCCCC[C@H](O)c1c(/C=C/[C@@H](O)[C@@H](O)C/C=C\CCC(=O)OC)nc(C)n1C] | methyl (4Z,7S,8R,9E)-7,8-dihydroxy-10-(5-((S)-1-hydroxyhexyl)-1,2-dimethyl-1H-imidazol-4-yl)deca-4,9-dienoate |
| I-2 | 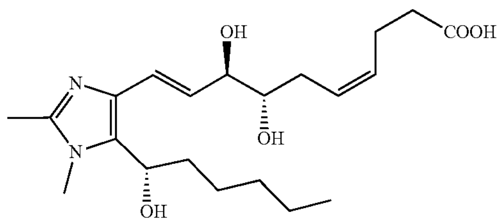 [SMILES: CCCCC[C@H](O)c1c(/C=C/[C@@H](O)[C@@H](O)C/C=C\CCC(=O)O)nc(C)n1C] | (4Z,7S,8R,9E)-7,8-dihydroxy-10-(5-((S)-1-hydroxyhexyl)-1,2-dimethyl-1H-imidazol-4-yl)deca-4,9-dienoic acid |

In some embodiments, the compounds of the present application have the Formula (IA):

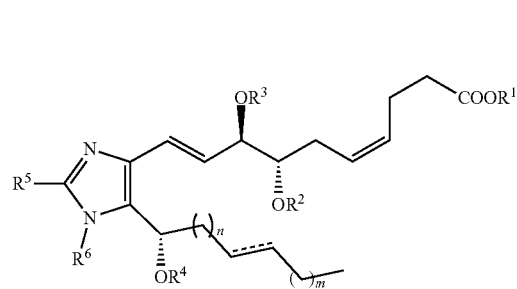

(IA)

wherein n and m are independently an integer from 0 to 7.

In some embodiments, the compounds of the present application have the Formula (IB)

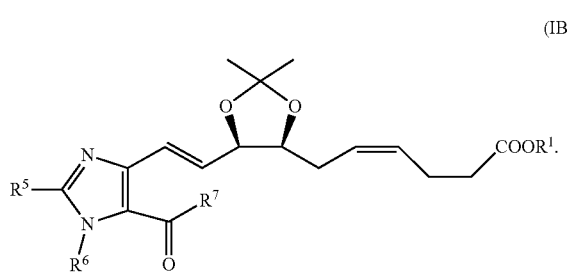

(IB)

In some embodiments, the compounds of the present application have the Formula (IC)

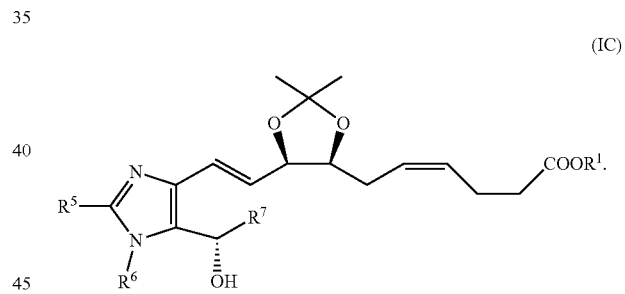

(IC)

III. Methods and Uses of the Application

The compounds of the application have been shown to inhibit TNFα production, inhibit monocytes/macrophages differentiation and protect against free radicals. Inflammation and oxidative stress are known to be involved in various diseases, such as arthritis, osteoarthritis, osteoporosis, etc.

Accordingly, the present application includes use of the compounds of the present application in treatment or prevention of an inflammatory disease or disorder. In some embodiments, the inflammatory disease or disorder is selected from arthritis, osteoarthritis, inflammatory bowel disease or disorder, and skin inflammatory disease or disorder. In some embodiments, inflammatory bowel disease or disorder may include Crohn's disease and ulcerative colitis. In some embodiments, skin inflammatory disease or disorder may include eczema, psoriasis, urticaria, and the like.

Accordingly, also provided is a method for the treatment or prevention of an inflammatory disease or disorder by administering an effective amount of a compound of the present application.

The present application further includes use of the compounds of the present application in treatment or prevention of a bone disease or disorder or joint disease and disorder. In some embodiments, the bone disease or disorder is selected from osteoporosis and bone metastases, and the joint disease or disorder is osteoarthritis.

Accordingly, also provided is a method for the treatment or prevention of a bone disease or disorder or joint disease and disorder by administering an effective amount of a compound of the present application.

Also included is a method for inhibiting osteoclasts recruitment, comprising administering an effective amount of a compound of the present application.

Provided is a method for inhibiting hyaluronic acid resorption, comprising administering an effective amount of a compound of the present application.

Further included is a method for inhibiting MMP-13 production, comprising administering an effective amount of a compound of the present application.

Also provided is a method for inhibiting ultraviolet-induced hyaluronic acid degradation, comprising administering an effective amount of a compound of the present application.

A method for inhibiting COX-2 expression, comprising administering an effective amount of a compound of the present application is also included.

Further included is use of the compounds of the present application as an antioxidant agent, a stabilizing agent or a preservative.

Antioxidant agents have many industrial applications and have a wide range of use in the preparation of several formulations. Thus, antioxidant agents are generally used as preservatives and supplements with the ultimate goal of stabilizing and increasing the shelf life of industrial products. This includes food products, cosmetics and medical products and petrochemicals. Typical preservatives include natural antioxidants such as sorbitol, mannitol, ascorbic acid, tocopherols, as well as synthetic antioxidants generally including phenolic compounds such as butylhydroxytoluene (BHT), tertiary butylhydroquinone (BHQ) or even gallates.

Specifically, the antioxidant properties of the compounds of the present application have been demonstrated in hyaluronic acid formulations (see Example 5).

Accordingly, the compounds of the present application may be used as an antioxidant agent, a stabilizing agent or a preservative in a food composition, a cosmetic composition, a pharmaceutical composition, a petrochemical composition or a medicinal composition.

Also included is use of a compound of the present application for inhibiting osteoclasts recruitment in a subject in need thereof.

Provided is use of a compound of the present application for inhibiting hyaluronic acid re-sorption in a subject in need thereof.

Further included is use of a compound of the present application for inhibiting MMP-13 production in a subject in need thereof.

Further provided is use of a compound of the present application for inhibiting ultraviolet-induced hyaluronic acid degradation in a subject in need thereof.

The present applicant further includes a method for stabilizing or preserving a composition, comprising adding an acceptable amount of a compound of the present application as an antioxidant agent, a stabilizing agent or a preservative, wherein the composition is an agri-food composition, a cosmetic composition, a pharmaceutical composition, a petrochemical composition or a medicinal composition.

IV. Methods of Preparing the Compounds and Compositions of the Application

The compounds of the present application can be prepared according to various synthetic routes within the purview of a skilled person in the art. In some embodiments, the compounds of the present application are prepared as described in the following Examples.

EXAMPLES

The following non-limiting examples are illustrative of the present application.
General Methods Reagents and solvents were obtained from commercial suppliers (Sigma Aldrich, Combi-blocks, Alfa Aesar) and used without further purification, unless otherwise noted. All reactions that were moisture and air-sensitive were carried out in flame-dried glassware, under an argon atmosphere. Reaction progress was monitored by thin layer chromatography (TLC), using EMD silica gel 60 F254 aluminum plates. Spots were visualized with UV light (254 nm), followed by staining using a cerium ammonium molybdate (CAM) solution or a potassium-permanganate solution, followed by heating on a hot plate. SiliCycle® R10030B 230-400 mesh silica gel (Quebec, QC, Canada) was used for flash chromatography. Nuclear magnetic resonance (NMR) spectra were recorded on a Bruker Avance 400 digital spectrometer (Billerica, MA, USA) at 400 MHz for $^1$H NMR. The following abbreviations were used to designate multiplicities: s=singlet, d=doublet, t=triplet, q=quartet, quint=quintuplet, m=multiplet, br=broad. Low-resolution mass spectra (MS) were recorded on a Shimadzu Prominence instrument (Kyoto, Japan) equipped with a Shimadzu LCMS-2020 mass spectrometer and an APCI (atmospheric pressure chemical ionization) probe. Molecule nomenclature (IUPAC) was generated using the ACD/name module of ACD/Labs software (Toronto, ON, Canada).

RvD1 analogs, in which one saturation in the tetraene unit of RvD1 has been replaced by an imidazole ring to increase chemical stability, have been prepared by assembling two building blocks A and B, as shown in general Scheme 1 below. The vinyl boronate block A containing two stereogenic centers and two double bonds (E, Z) of RvD1, was prepared in 5 steps from enantiomerically pure D-deoxyribose, but other stereochemistry are contemplated. Different $R^1$ groups may be used using the same procedure. On the other hand, block B was obtained from 1,2-$R^5R^6$-imidazole in 1 step. Different $R^5$ and $R^6$ groups may be used using the same procedure. Suzuki cross coupling reaction between block A and block B afforded a 3,4-disubstituted imidazole intermediate. Subsequent reduction of the ketone followed by deprotection of the alcohol-protecting groups provide for RvD1 analogs, according to embodiments of the present application.

Scheme 1

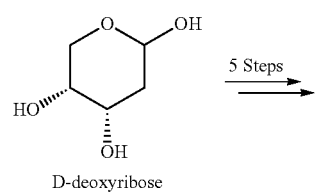

D-deoxyribose

5 Steps →

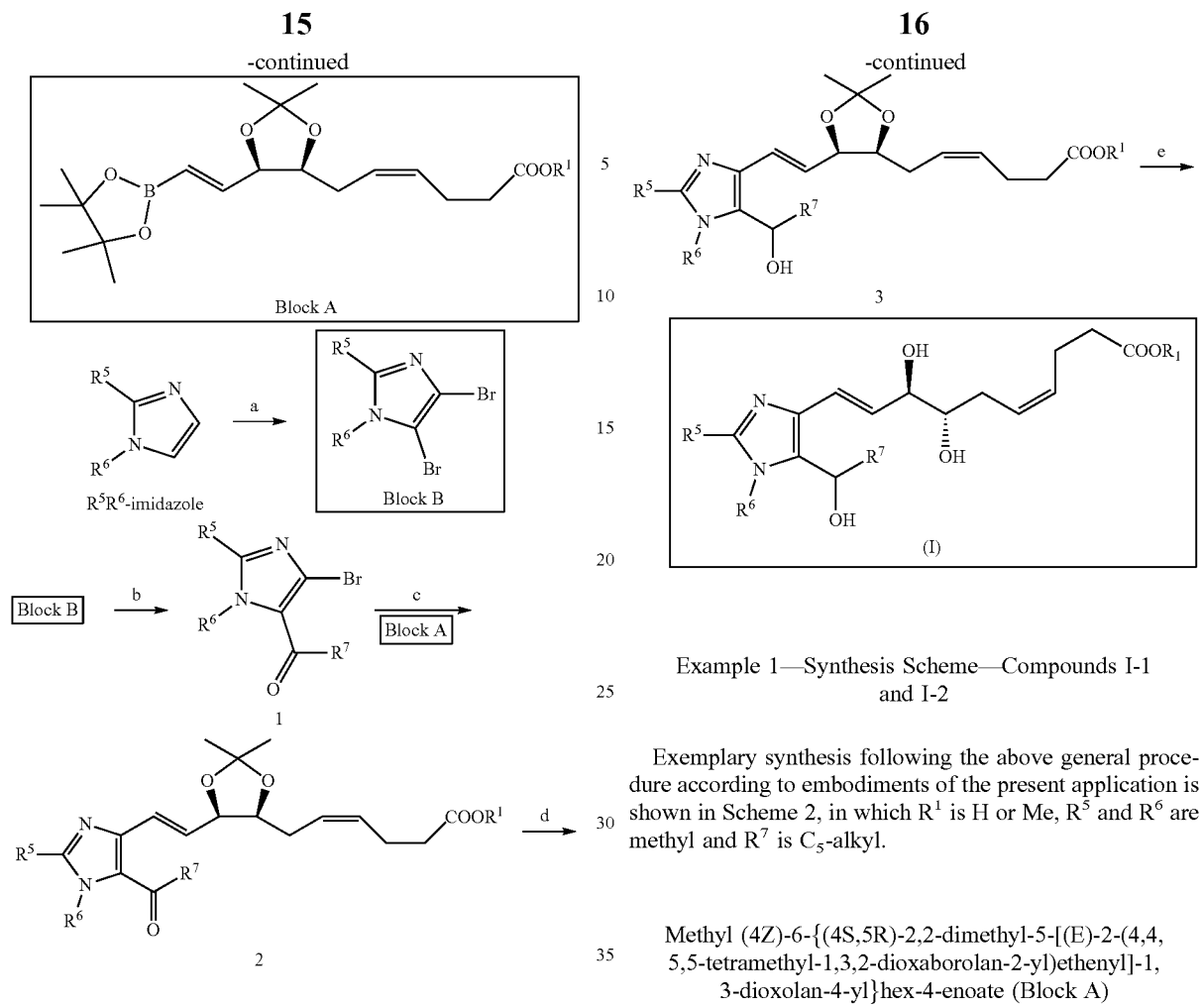
Example 1—Synthesis Scheme—Compounds I-1 and I-2
Exemplary synthesis following the above general procedure according to embodiments of the present application is shown in Scheme 2, in which $R^1$ is H or Me, $R^5$ and $R^6$ are methyl and $R^7$ is $C_5$-alkyl.
Methyl (4Z)-6-{(4S,5R)-2,2-dimethyl-5-[(E)-2-(4,4,5,5-tetramethyl-1,3,2-dioxaborolan-2-yl)ethenyl]-1,3-dioxolan-4-yl}hex-4-enoate (Block A)
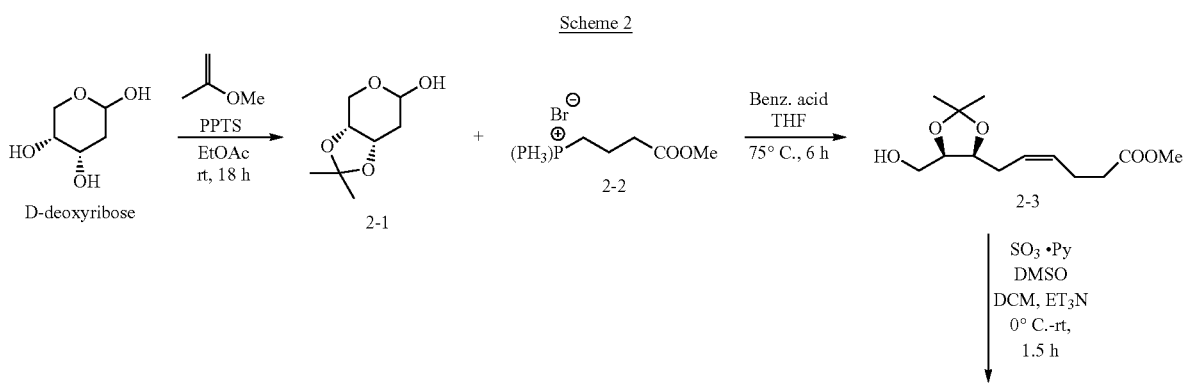
Scheme 2

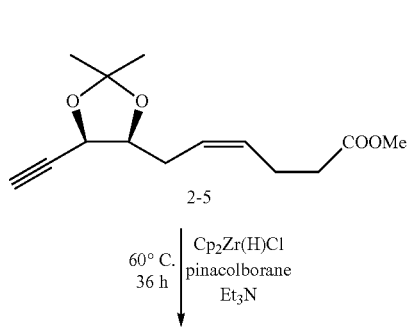

2-5

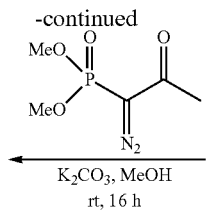

K₂CO₃, MeOH
rt, 16 h

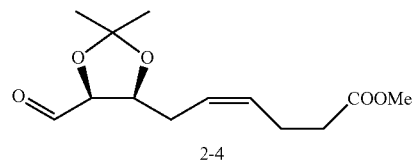

2-4

60° C.
36 h | Cp₂Zr(H)Cl
pinacolborane
Et₃N

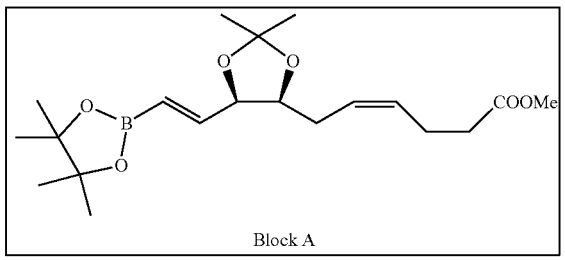

Block A

The block A was prepared following the five steps synthetic sequence reported by Gaetano et al. (ref: European Journal of Medicinal Chemistry, 2019,162, 80-108), as shown in Scheme 2.

D-deoxyribose was treated with 2-methoxyprop-1-ene in ethyl acetate in the presence of a catalytic amount of pyridinium p-toluenesulfonate (PPTS). The mixture was reacted at room temperature for 18 h to afford intermediate 2-1. Intermediate 2-1 was treated with phosphonium salt 2-2 and benzoic acid in THF. The mixture was heated at 75° C. for 6h to give intermediate 2-2. Intermediate 2-3 was then treated with sulfur trioxide pyridine complex and DMSO, in the presence of TEA, and DCM at 0° C. The mixture was allowed to warm to room temperature for about 1.5h to provide oxidated intermediate 2-4. Intermediate 2-4 was then treated with dimethyl(1-diazo-2-oxopropyl)phosphonate in methanol in the presence of K₂CO₃ and reacted at room temperature for 16h to give intermediate 2-5. Finally, intermediate 2-5 was treated with pinacolborane, TEA and Schwartz's reagent (zirconocene hydrochloride) to afford the boronate compound—Block A. Between each step, reactions were quenched and compounds isolated and/or purified before proceeding to following step. ¹H NMR data were in full agreement with that reported in the literature.

4,5-dibromo-1,2-dimethyl-1H-imidazole (Block B)

Scheme 3

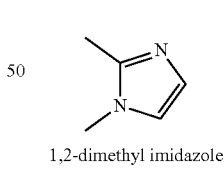

1,2-dimethyl imidazole

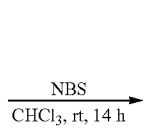

NBS
CHCl₃, rt, 14 h

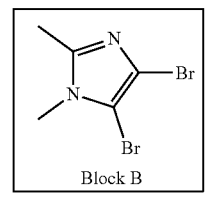

Block B

This compound was prepared following a literature procedure (ref: European Journal of Medicinal Chemistry 2019, 162, 80-108), as shown in Scheme 3. 1,2-dimethylimidazole was treated with N-bromosuccinimide (2.2 eq) in chloroform and reacted for 14 h at room temperature to give the dibromo-imidazole compound—Block B. Reaction was quenched and compound isolated and/or purified. ¹H NMR data were in full agreement with that reported in the literature.

Blocks A and B were used in the following synthesis, as shown in Scheme 4:

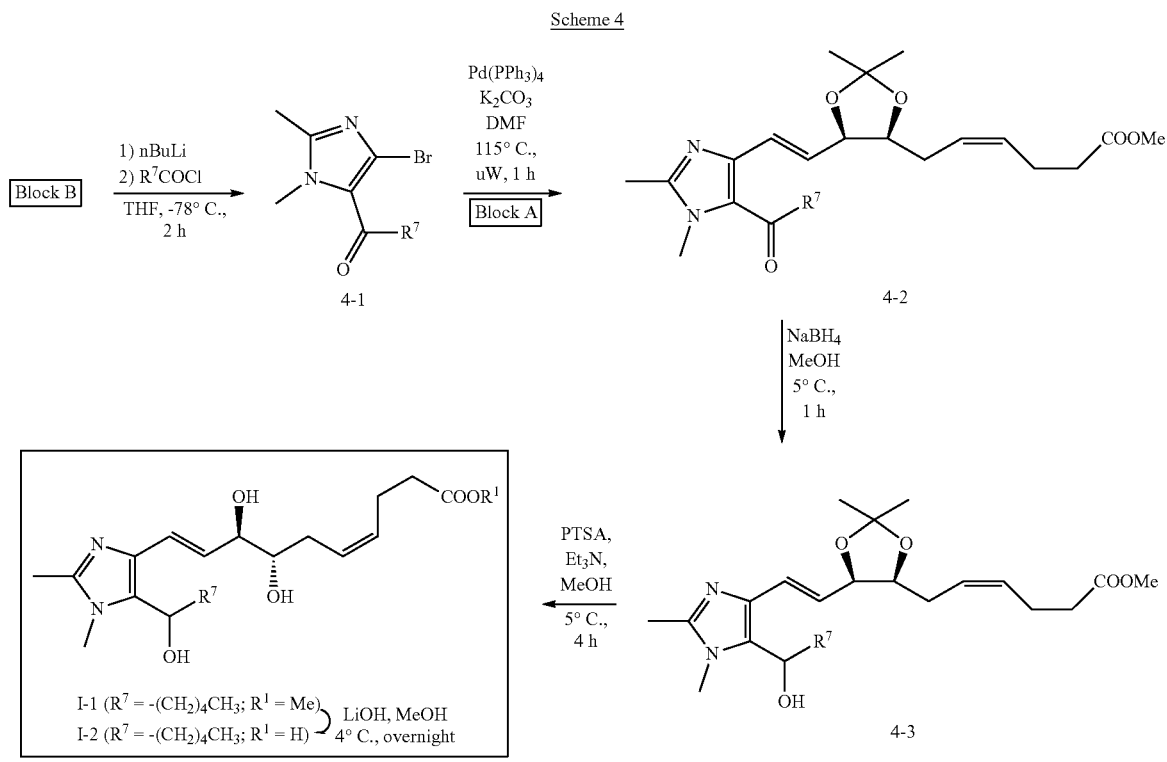

Scheme 4

1-(4-bromo-1,2-dimethyl-1H-imidazol-5-yl)hexan-1-one (4-1)

This compound was prepared following a literature procedure (ref: European Journal of Medicinal Chemistry 2019, 162, 80-108). $^1$H NMR data were in full agreement with that reported in the literature.

Methyl (4Z)-6-{(4S,5R)-5-[(E)-2-(5-hexanoyl-1,2-dimethyl-1H-imidazol-4-yl)ethenyl]-2,2-dimethyl-1,3-dioxolan-4-yl}hex-4-enoate (4-2)

In a 5 mL microwave vial, compound 4-1 (20 mg, 0.074 mmol) and Block A (34 mg, 0.089 mmol) were solubilised in DMF (2 mL) and 2M $K_2CO_3$ (0.1 mL). Argon was bubbled through the mixture for 15 min before addition of $Pd(PPh_3)_4$ (10 mg. 0.008 mmol). After sealing, the tube was heated in a microwave apparatus at 115° C. for 1 h. After cooling at room temperature, water was added and the aqueous phase extracted with EtOAc. The combined extracts were washed with water, brine and dried over $Na_2SO_4$. The residue was purified on silica gel eluting with EtOAc in hexanes (5% to 100%) affording compound 4-2 (8 mg). $^1$H NMR shows contamination with triphenylphosphine oxide and (1,2-dimethyl-1H-imidazol-5-yl)hexan-1-one. $^1$H NMR (400 MHz, Methanol-$d_4$) δ 6.86 (d, J=15.3 Hz, 1H), 6.43 (dd, J=15.3, 6.8 Hz, 1H), 5.33 (m, 2H), 4.68 (m, 1H), 4.21 (q, J=6.6 Hz, 1H), 3.65 (s, 3H), 3.49 (s, 3H), 2.29 (s, 3H), 2.18 (s, 6H), 1.58 (m, 2H), 1.41 (s, 3H), 1.26 (m, 7H), 0.81 (bs, 3H).

Methyl (4Z)-6-[(4S,5R)-5-{(E)-2-[5-(1-hydroxyhexyl)-1,2-dimethyl-1H-imidazol-4-yl]ethenyl}-2,2-dimethyl-1,3-dioxolan-4-yl]hex-4-enoate (4-3)

To an ice-cooled solution of compound 4-2 (8 mg) in MeOH (0.5 mL) was added $NaBH_4$ (2 mg). The mixture was stirred at 5° C. for 1 h then quenched with a 10% aqueous solution of $NaH_2PO_4$. The aqueous phase was extracted twice with EtOAc. The combined extracts were washed with water, brine and dried over $Na_2SO_4$. Evaporation gave crude compound 4-3 (9 mg). $^1$H NMR (400 MHz, Methanol-$d_4$) δ 6.59 (d, J=15.6 Hz, 1H), 6.21 (dd, J=15.6, 8.1 Hz, 1H), 5.43 (m, 2H), 4.68 (m, 1H), 4.21 (m, 1H), 3.65 (s, 3H), 3.62 (s, 3H), 2.30 (s, 3H), 2.18 (s, 3H), 1.92 (m, 1H), 1.76 (m, 1H), 1.49-1.19 (m, 12H), 0.88 (bs, 3H).

Methyl (4Z,7S,8R,9E)-7,8-dihydroxy-10-[5-(1-hydroxyhexyl)-1,2-dimethyl-1H-imidazol-4-yl]deca-4,9-dienoate (I-1)

Figure 6:
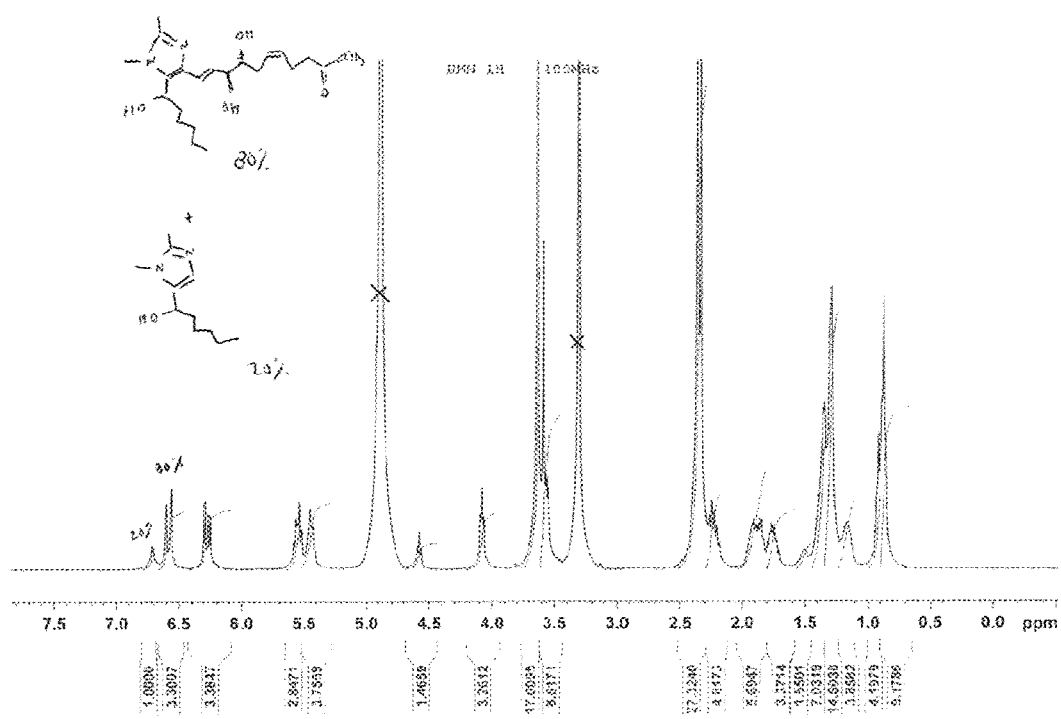
FIG. 6 shows a $^1$NMR spectra for compound I-1, according to exemplary embodiments of the present application.
Figure 7:
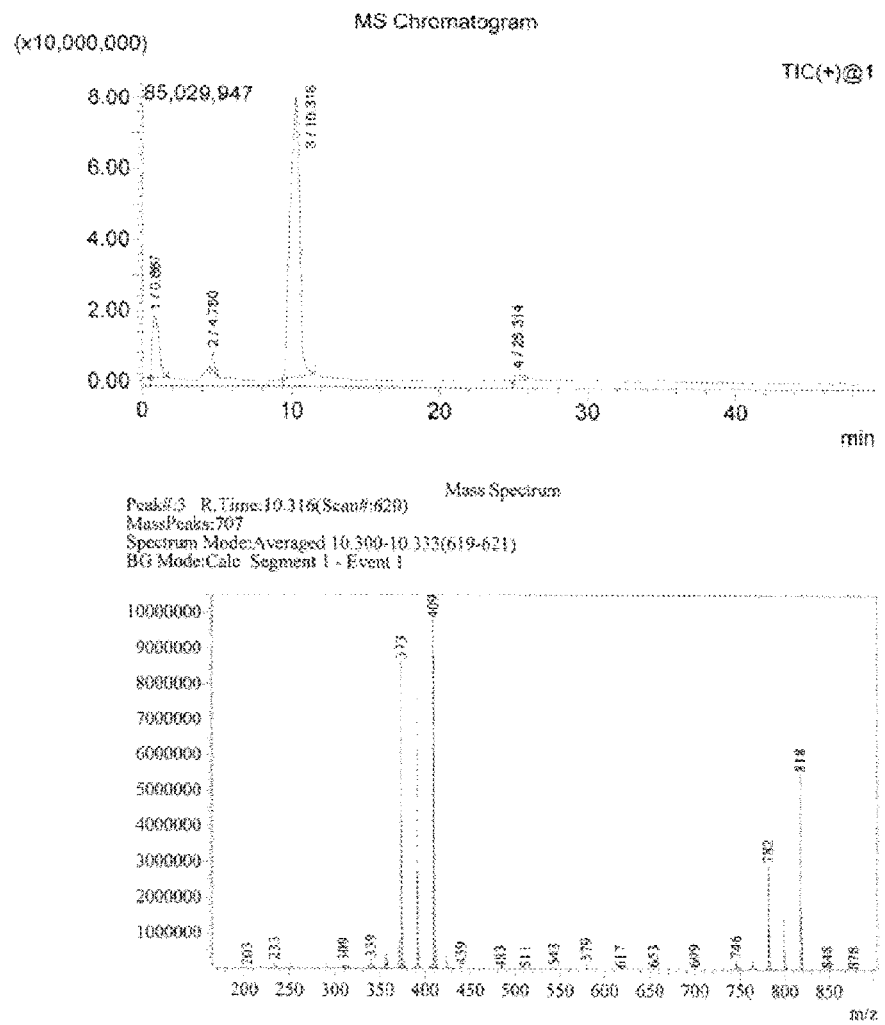
FIG. 7 shows a LCMS chromatogram for compound I-1, according to exemplary embodiments of the present application.

To a solution of crude compound 4-3 in MeOH (2.5 mL) was added pTSA (10 mg) at 5° C. and stirred for 4 h. Triethylamine was added and MeOH was evaporated under reduce pressure. The residue was poured into water and extracted with EtOAc. The combined extracts were washed with water, brine, dried over $Na_2SO_4$, filtered and evaporated under reduced pressure to give crude compound I-1. This later compound was purified by preparative TLC using DCM/MeOH (9:1) as eluent to give 4.8 mg of compound I-1. $^1$H NMR (400 MHz, Methanol-$d_4$) δ 6.58 (d, J=15.7 Hz, 1H), 6.27 (dd, J=15.1, 7.3 Hz, 1H), 5.55 (m, 1H), 5.45 (m, 1H), 4.58 (m, 1H), 4.08 (m, 1H), 3.64 (s, 3H), 3.59 (s, 3H), 2.37 (m, 3H), 1.93-1.71 (m, 2H), 1.49-1.17 (m, 12H), 0.88 (bs, 3H). MS (APCI pos) m/z 409.3 [M+H]. NMR spectra and LCMS chromatogram are shown in FIG. 6 and FIG. 7, respectively.

(4Z,7S,8R,9E)-7,8-dihydroxy-10-[5-(1-hydroxy-hexyl)-1,2-dimethyl-1H-imidazol-4-yl]deca-4,9-dienoic acid (1-2)

Figure 8:
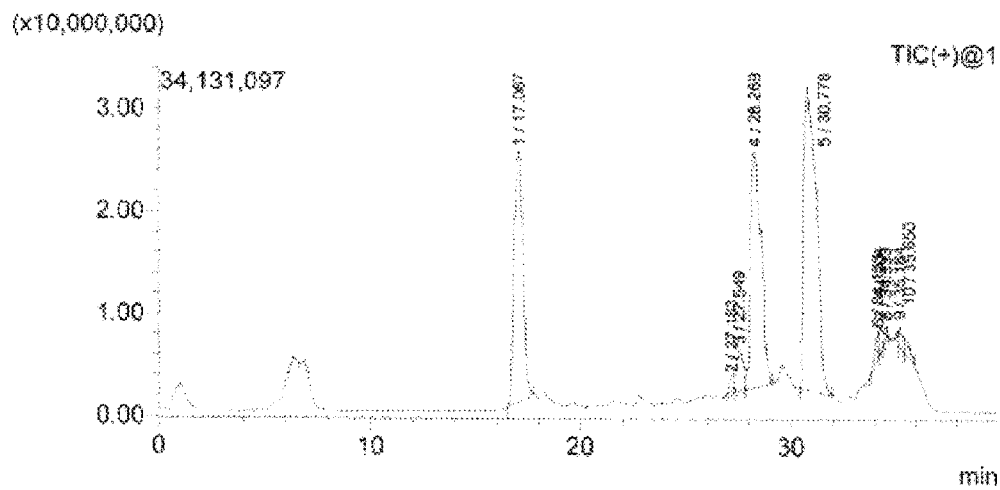
FIG. 8 shows a LCMS chromatogram for compound 1-2, according to exemplary embodiments of the present application.
Figure 8:
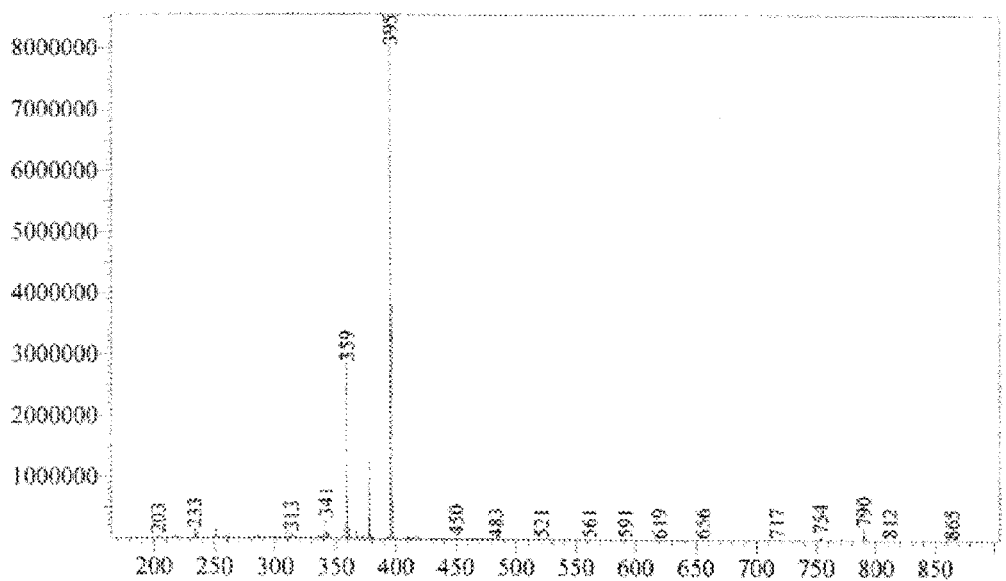

To a solution of compound I-1 (2.4 mg, 0.006 mmol) in MeOH (0.5 mL) was added LiOH (15 mg, 0.6 mmol). The mixture was stirred at 4° C. overnight and then poured into aqueous solution (10%) of $NaH_2PO_4$. The aqueous solution was extracted with EtOAc, washed with brine, dried over sodium sulfate, filtered and evaporated under reduce pressure to give 1.0 mg of compound 1-2. MS (APCI pos) m/z 395.3 [M+H]. LCMS chromatogram is shown in FIG. 8.

Example 2—Cell Culture

Murine macrophage RAW 264.7 (ATCC, Manassas, VA, USA) were cultured with AMEM/10% FBS and antibiotics at 37° C. in a humidified atmosphere with 5% $CO_2$. Primary human monocytes were isolated from whole blood obtained from healthy volunteers. Briefly, blood was centrifuged on a Ficoll-Paque density gradient, according to the manufacturer's recommendations. Isolated monocytes were then cultured in RPMI 1640 medium supplemented with 10% FBS, and antibiotics. All donors provided written, informed consent for the use of their blood for research purposes. Experimental protocols were approved by the Research Ethics Board of the "Hôpital du Sacré-Coeur de Montreal".

Example 3—Cell Viability Assay

Raw264.7 cells were treated for 24 hours with increasing concentrations of compounds I-1 and I-2 (0, 0,1, 0,25, 0,5, and 1 µM). Cell viability was assessed with MTS assay kit (Promega Corporation, Madison, WI, USA), as described by the manufacturer. Absorbance was measured with the micro-ELISA Vmax photometer (Bio-Tek Instruments, Winooski, VT, USA). Cell viability was evaluated by 3-(4,5-dimethyl-thiazoyl)-2,5-diphenyl-SH-tetrazolium bromide assay. ANOVA test was performed to compare the results. Results are expressed as mean±SEM for n=3. Results are shown in FIG. 1.

Example 4—TRAP Staining

Figure 3:
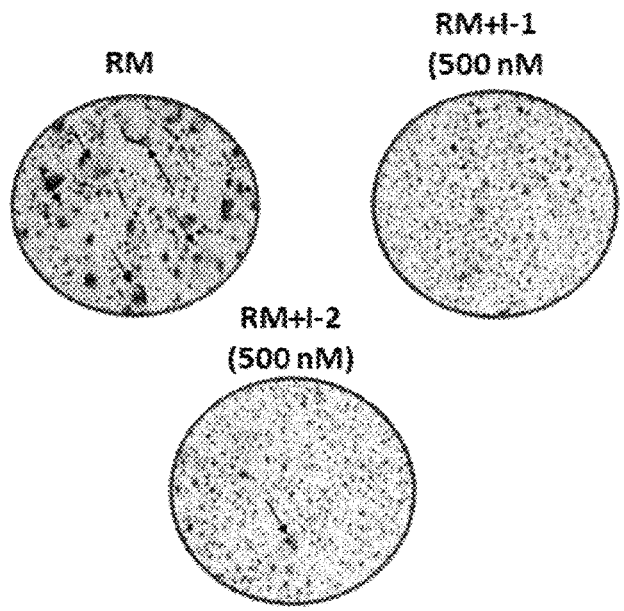
FIG. 3 shows images of TRAP enzymatic staining on isolated human monocytes for compounds 1-1 and 1-2 treatment (500 nM) for 14 days, according to exemplary embodiments of the present application.

Isolated human monocytes were isolated as described previously, seeded in chambered cell culture slides at $8 \times 10^4$ cells/well, and treated with 50 ng/ml RANKL and 10 ng/ml M-CSF in the presence or absence of 500 nM of compounds I-1 and I-2 for 14 days. Culture medium was changed every 3 days. TRAP staining performed as recommended by the manufacturer. Nuclei were counter stained with Gill's hematoxylin and TRAP positive multinucleated osteoclasts staining ($\geq 3$ nuclei) was counted in 10 randomly selected high-power fields using digital EVOS™ light microscopy (Electron Microscopy Sciences, Hatfield, PA, USA) at 20× magnification, and TRAP-positive cells were observed with an inverted microscope (×200). Results are shown in FIG. 3, where arrows show osteoclasts with three nuclei or more (b). R=RANKL; M=M-CSF.

Example 5—Hyaluronic Acid Degradation

Figure 4:
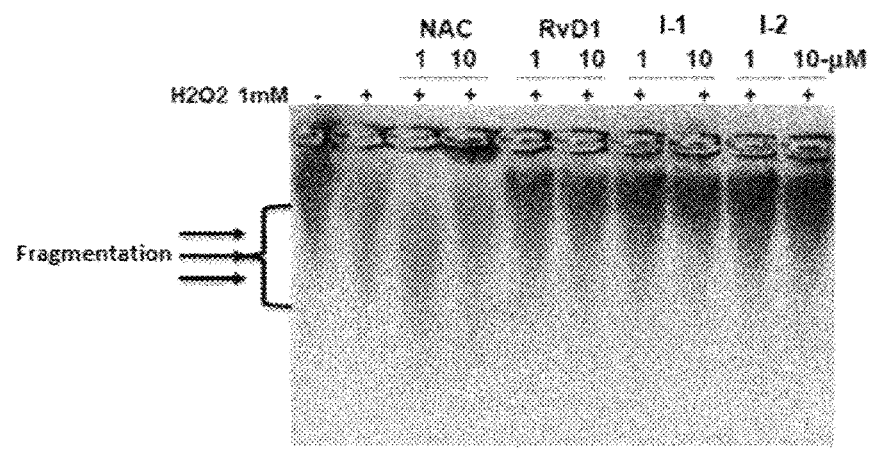
FIG. 4 shows differential staining images of hyaluronic acid degradation for RvD1, compounds 1-1 and 1-2, according to exemplary embodiments of the present application.

Commercial hyaluronic acid was solubilised in sterilized PBS (1 mg/ml) during overnight under gentile shaking. The solution was pretreated with N-acetyl-Cysteine (NAC), RvD1, compounds I-1 and I-2 at 1 or 10 µM for 1 hour and then treated with 1 mM $H_2O_2$ during 4 hours. Samples were mixed in loading buffer containing 1M sucrose and loaded in 1% agarose/1× Tris-borate-EDTA (TBE) and pre-run the gel for 6 hours at 40V in 1× TBE buffer. The gel was then equilibrated with 30% ethanol in water and stained with Stains-All solution containing 0.1 mg Stains-All and 30% ethanol for overnight in the dark. Next, the gel was equilibrated in water for 1 hour and then exposed to light for destaining. Finally, hyaluronic acid was visualized using Alpha Imager under light transillumination. Results are shown in FIG. 4, where arrows show hyaluronic acid fragments (n=2), A1=I-1; A2=I-2.

Example 6—Protein Detection by Western Blotting

Figure 5:
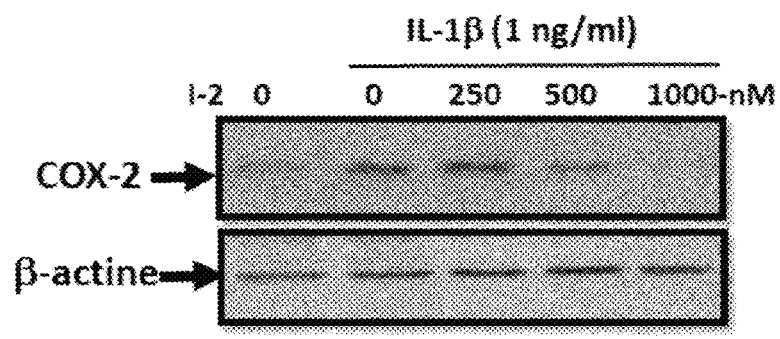
FIG. 5 shows image of a Western blotting of protein detection of Raw264.7 macrophages lysates for compound 1-2, according to exemplary embodiments of the present application.

20 µg of total proteins of Raw264.7 macrophages lysates, treated under the indicated conditions, were loaded for discontinuous 4-12% sodium dodecyl sulfate-polyacrylamide gel electrophoresis. They were then transferred electrophoretically onto nitrocellulose membranes (Bio-Rad Laboratories, Mississauga, ON, Canada) for protein immunodetection and semi-quantitative measurement. The primary antibodies deployed were rabbit anti-COX-2 (Cayman Chemical Company) and mouse anti-β-actine (Sigma). After serial washes, the primary antibodies were revealed by goat anti-mouse or anti-rabbit immunoglobulin G conjugated to horseradish peroxidase (Cell Signaling Technology, Inc.). Immunoreactive proteins were detected with Super-Signal blotting substrate (Pierce, Rockford, IL) and exposed to Kodak X-Omat™ film (Eastman Kodak Company, Rochester, NY). Results for compound 1-2 are shown in FIG. 5.

Results

Cytotoxicity in Raw 264.7 Macrophages

This part of the experiment was designed to test the cytotoxic effect of compounds 1-1 and 1-2 on mouse Raw264.7 macrophages. As illustrated in FIG. 1°, the two analogues at different concentrations (0, 0.1, 0.25, 0.5, and 1-µM) did not alter the cell viability after 24 h of incubation. As such, it may be concluded that compounds I-1 and I-2 were not cytotoxic in Raw 264.7 macrophages.

Inhibition of TNFα Production

Figure 2:
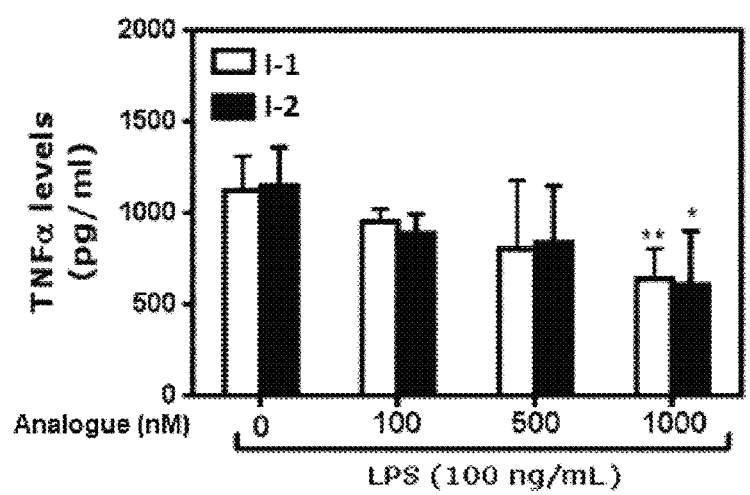
FIG. 2 shows a graph of TNFα levels RvD1 in Raw264,7 macrophages for compounds 1-1 and 1-2 at increasing doses (0, 0,1, 0,5, and 1-mM), according to exemplary embodiments of the present application.

It is well-documented that the RvD1 is considered as a potent anti-inflammatory mediator. Thus, the purpose of this part of the present study was to investigate whether compounds I-1 and I-2's capacity to inhibit pro-inflammatory cytokines, such as TNFα. To do so, Raw264.7 were pretreated with compounds I-1 and I-2 at different concentrations (0, 0.1, 0.5, and 1-µM) for 1h, followed by exposure to 1 ng/ml IL-1β for 24 h. As illustrated in FIG. 2, escalating doses of RvD1 analogues blocked IL-1β-induced TNFα production. compounds I-1 and I-2 at 1-µM reduced TNFα level by 40%, as compared to cells treated with IL-1β alone. As such, it may be concluded that compounds I-1 and I-2 inhibit TNFα production.

Osteoclast Differentiation

Here, the impact of RvD1 analogues treatment on human isolated monocytes/macrophages-RANKL/M-CSF-derived osteoclasts was eveluated, by measuring their phenotypic markers, namely TRAP. As shown in FIG. 3, the addition of compounds I-1 and I-2 at 500 nM to the cultured cells strongly prevent osteoclasts differentiation as compared to RANKL/M-CSF-treated cells. As such, it may be concluded that compounds I-1 and I-2 inhibit monocytes/macrophages differentiation.

$H_2O_2$-Induced Hyaluronic Fragmentation

This part of experiments was designed to investigate the ability of RvD1 analogues to protect hyaluronic acid against $H_2O_2$-induced degradation (antioxidant effect). To do so, the polymer at 1 mg/ml was pretreated by RvD1 and their analogues for 1 hour and then after treated with 1 mM $H_2O_2$ for 4 hours. Results are shown in FIG. 4. The preliminary data showed that RvD1, compounds I-1 and I-2 prevent $H_2O_2$-induced fragmentation. These findings suggest the potential use of RvD1 analogues for hyaluronic acid protection against free radical's attack.

COX-2 Protein Expression

Here, the hypothesis whether RvD1 analogues have the ability to modulate COX-2 protein expression was tested. Raw264.7 macrophages were pretreated with increasing doses of compound I-2 (0, 0.25, 0.5, 1-µM) for 1 hour and treated then after with 1 ng/ml IL-1β for 24 hours. As shown in FIG. 5, we revealed that compound I-2 reduced IL-1β-induced COX-2 protein expression (n=2), suggesting the anti-inflammatory properties of I-2.

Example 7—Effect of RvD1 Analogs on Osteoclast Recruitment

Figure 9:
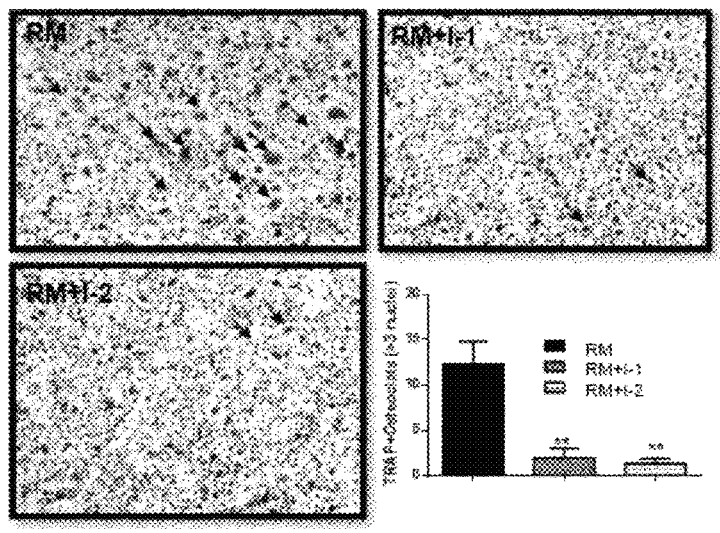
FIG. 9 shows results of the inhibition of osteoclasts differentiation by compounds 1-1 and 1-2, according to exemplary embodiments of the present application, where arrows show osteoclasts with three nuclei or more.

The effect of RvD1 analogs on the differentiation of macrophages into osteoclasts was investigated. Monocytes from peripheral blood of healthy donors were cultured in culture chambers at $2 \times 10^5$ monocytes/chamber in the presence of 50 ng/ml RANKL+10 ng/ml M-CSF for 14 days, in the presence or absence of 500 ng of compounds I-1 and I-2 (n=3). TRAP-positive cells were observed with an inverted microscope (×200). FIG. 9 shows that treatment of cells with RANKL+M-CSF (RM) induced the formation of osteoclasts (3 or more nuclei). On the other hand, the combination of RANKL+M-CSF with I-1 and I-2 inhibited the formation of large osteoclasts.

Example 8—Effect of RvD1 Analogs on Prevention of Bone Erosion

Figure 10:
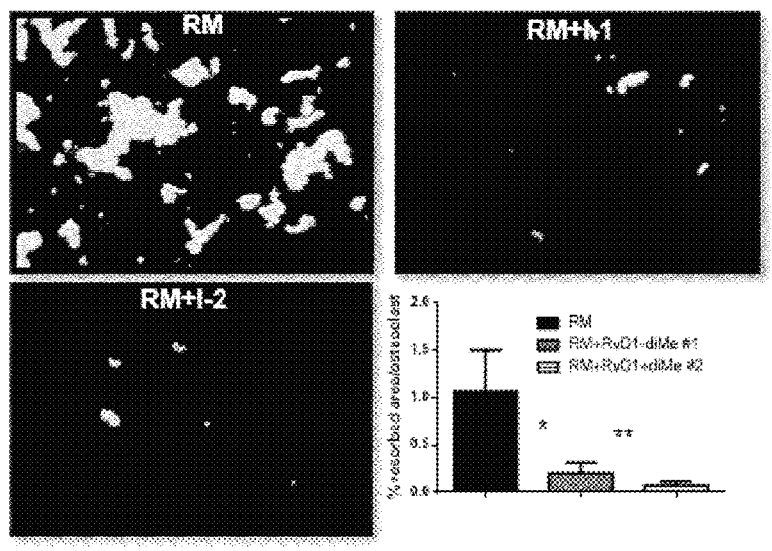
FIG. 10 shows results of the inhibition of hydroxyapatite matrix resorption by compounds 1-1 and I-2, according to exemplary embodiments of the present application.

The effect of RvD1 analogs on the resorption activity of human monocyte-derived osteoclasts was investigated. Results were obtained as described in Benabdoun et al. 2019 and are shown in FIG. 10, where data were expressed as % resorption area/osteoclast with three nuclei or more (n=3). As shown by von Kossa staining in FIG. 10, a significantly higher erosion area was observed when cells were differentiated into M-CSF/RANKL (R-M) compared to control, while compounds I-1 and O-2 at 500 nM significantly reduced erosion of the hydroxyapatite matrix to almost control level ($p<0.01$).

Example 9—Effect of RvD1 Analogs on MMP-13 Expression

Figure 11:
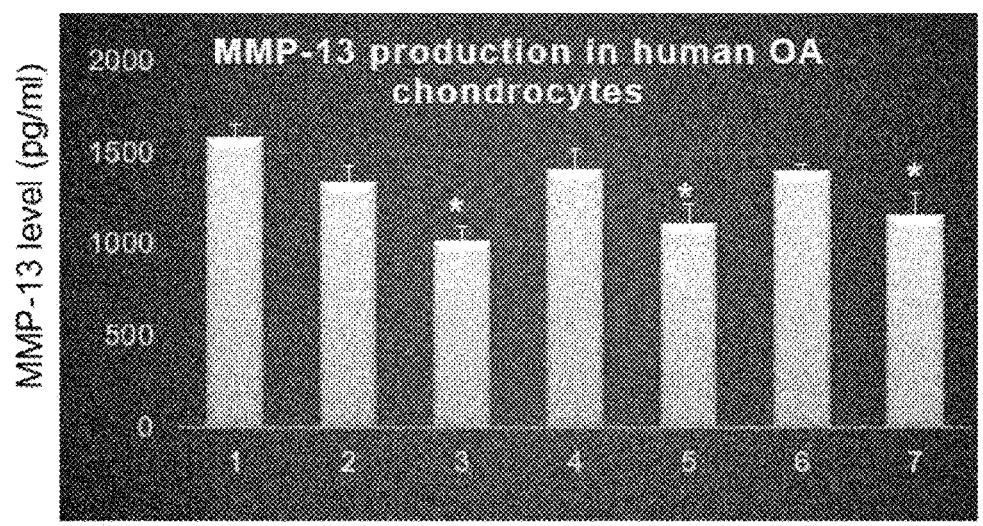
FIG. 11 shows results of the inhibition of MMP-13 production in human OA chondrocytes, according to exemplary embodiments of the present application, where 1: IL-1b; 2: RvD1 (1 μM), 3: RvD1 (10 μM), 4: I-1 (10 μM), 5: 1-1 (20 μM), 6: 1-2 (10 μM), 7: 1-2 (20 μM) and data are expressed as pg/ml (n=3), *p<0.05.

The effect of RvD1 analogs on the expression of MMP-13, a key enzyme involved in the degradation of OA cartilage, was investigated. Chondrocytes from human osteoarthritic cartilage were treated with IL-1β (1 ng/ml) for one hour followed by another treatment with RvD1 and its analogues for 24 hours. The results show RvD1 and compounds I-1 and I-2 inhibit MMP-13 production by approximately 20% at a concentration of 10 µM (RvD1) and 20 µM for I-1 and I-2 (FIG. 11). Without being bound to theory, the results show that the effect of the analogs on the expression of MMP-13 is significant at high doses.

Example 10—Effect of RvD1 Analogs on HA Stability

Figure 12:
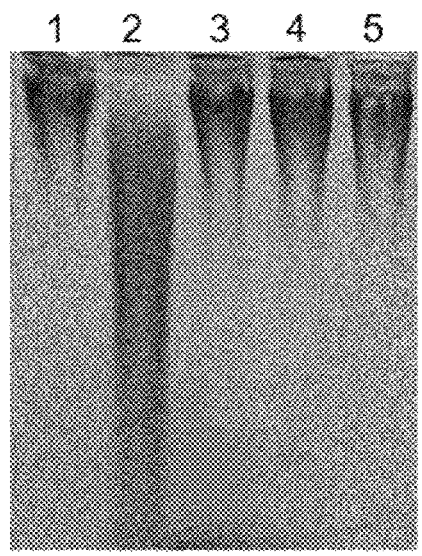
FIG. 12 shows results of the inhibition of ultraviolet(UV)-induced hyaluronic acid (HA) degradation, according to exemplary embodiments of the present application, where 1: HA Control, 2: HA+UV, 3: HA+UV+RvD1 (1 μM), 4: HA+UV+I-1 (1 μM), 5: HA+UV+I-2 (1 μM) (n=3).

In order to study the protective effect of RvD1 and its analogs on the stability of hyaluronic acid (HA), a solution of commercial HA was prepared in PBS at a concentration of 1 mg/ml, then exposed to Ultraviolet rays (UV) for 4 hours in the presence or absence of RvD1 and compounds I-1 and I-2 at a dose of 1 µM. 20 µg of HA were loaded into an agarose gel (1% prepared in TBE buffer). After 4 hours of migration at 40 volts, the HA was visualized after staining with Stains-All dissolved in 30% ethanol. As shown in FIG. 12, without being bound to theory, treatment of HA with RvD1 or compounds I-1 and I-2 prevents HA degradation by UV exposure.

Example 11—Studies of the Antioxidant Properties of RvD1 Analogs

Figure 13:
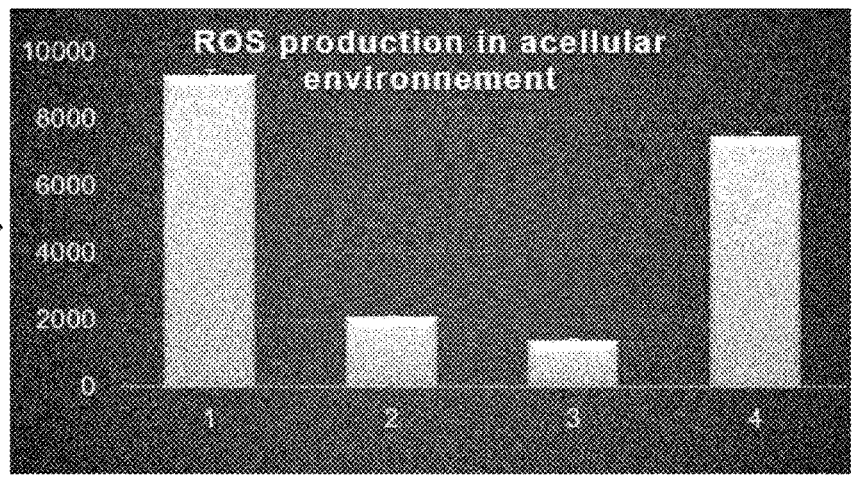
FIG. 13 shows results of the reactive oxygen species (ROS) production in acellular environment, according to exemplary embodiments of the present application, where 1: ROS (Positive CTL); 2: RvD1 (1 μM); 3: I-1 (1 μM), 4: I-2 (1 μM).

In a first step, it was attempted to demonstrate the ability of RvD1 and its analogs to neutralize oxygen free radicals (ROS) in an acellular medium. ROS were generated by incubating in black 96-well plate with $CuCl_2$ (1 mM) with $H_2O_2$ (1 mM) for 10 min. Subsequently, RvD1, I-1 and I-2 at 1 µM were added before the addition of the DCFH-DA probe. The results are shown in FIG. 13 and show that the level of ROS decreases in the presence of RvD1, I-1 and I-2. Without wishing to be bound to theory, these results suggest that RvD1 and its analogs scavenge free radicals in a cell-free environment.

Figure 14:
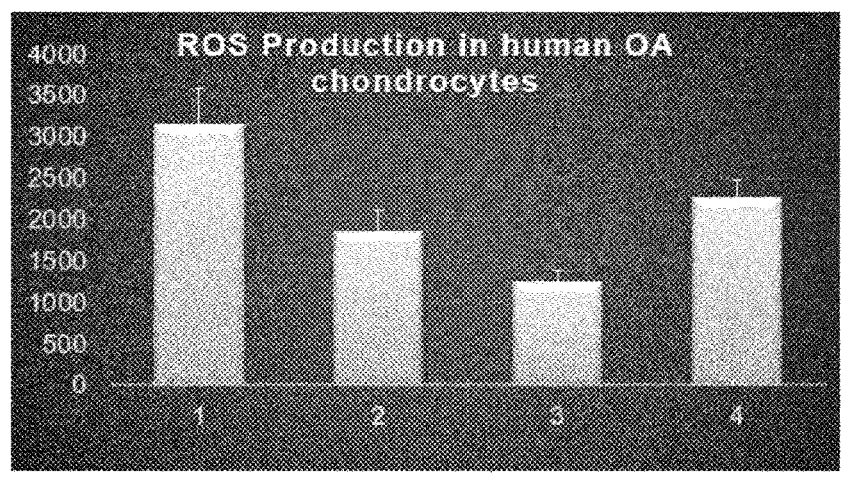
FIG. 14 shows results of the reactive oxygen species (ROS) production in human OA chondrocytes, according to exemplary embodiments of the present application, where 1: ROS (Positive CTL); 2: RvD1 (1 μM); 3: I-1 (1 μM), 4: I-2 (1 μM).

In a second step, the study was continued to explore the antioxidant effect of RvD1 and compounds I-1 and I-2 in a cell medium. Thus, human OA chondrocytes with osteoarthritis were seeded in black plates at a rate of $5 \times 10^4$ cells per well in 10% FBS DMEM medium (phenol red free) and incubated for 24 h at 37° C., and then treated with 0.5 mM $H_2O_2$ for 2 hours in the presence or absence of RvD1 and the compounds I-1 and I-2 at a concentration of 1 µM. The generation of ROS was measured by the addition of 10 µM of the DCFH-DA probe and fluorescence was measured using a microplate reader with Fluorescence Polarization (Polar Star Optima, BMG Labtech) set up at ex. 485 nm and em. 530 nm. The results are shown in in FIG. 14 which illustrates that treatment with RvD1, I-1 and I-2 significantly reduced the generation of ROS by chondrocytes. Without wishing to be bound to theory, these data suggest an antioxidant effect of our analogues.

Figure 15:
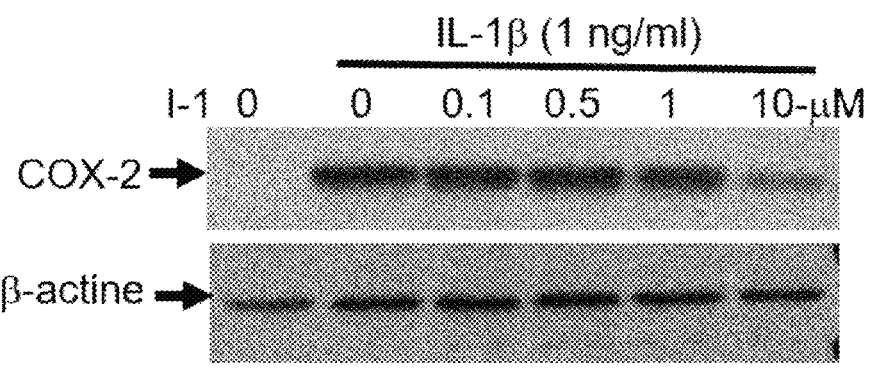
FIG. 15 shows results of the effect compound I-1 on COX-2 expression in human OA chondrocytes, according to exemplary embodiments of the present application.

Example 12—Effect of Compound I-1 on COX-2 Expression in OA Chondrocytes with Osteoarthritis Cells were seeded in 24-well flat plates at a confluence of $5 \times 10^5$ cells per well in 10% FBS DMEM medium and incubated for 24 h at 37° C. Then, the cells were treated with I-1 at different doses (0-10 µM) for 1 hour followed by a second treatment with IL-1β for 24 hours (1 ng/ml). COX-2 expression was assessed by Western blot by specific anti-COX-2 antibody. The results shown in FIG. 15 reveal that analog I-1 reduces COX-2 expression at a concentration of 10 µM.

While the applicant's teachings described herein are in conjunction with various embodiments for illustrative purposes, it is not intended that the applicant's teachings be limited to such embodiments as the embodiments described herein are intended to be examples. On the contrary, the applicant's teachings described and illustrated herein encompass various alternatives, modifications, and equivalents, without departing from the embodiments described herein, the general scope of which is defined in the appended claims.

The invention claimed is:

1. A compound of Formula (I):

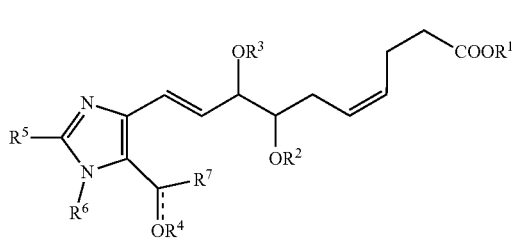

wherein
- $R^1$ is selected from the group consisting of H and $C_{1-8}$ alkyl;
- $R^2$, $R^3$ and $R^4$ are independently selected from the group consisting of H, $C_{1-8}$ alkyl, and a suitable protecting group; wherein $R^2$ and $R^3$ may be joined to form, together with the atom therebetween, an heterocyclyl group;
- $R^5$ and $R^6$ are independently selected from the group consisting of H and $C_{1-8}$ alkyl;
- $R^7$ is selected from the group consisting of linear or branched $C_{1-10}$ alkyl and linear or branched $C_{2-10}$ alkenyl, wherein the alkyl and alkenyl may be interrupted by 1 to 3 heteroatoms selected from O, N and S, and may be substituted with one or more group selected from halogen, —OH, —$CF_3$, —CN, —$NH_2$, —SH and phenyl,
- ⌇ is absent or represents a bond, wherein $R^4$ is absent when ⌇ is a bond,
or an enantiomer, isomer, salt or solvate thereof.

2. A compound of Formula (IA):

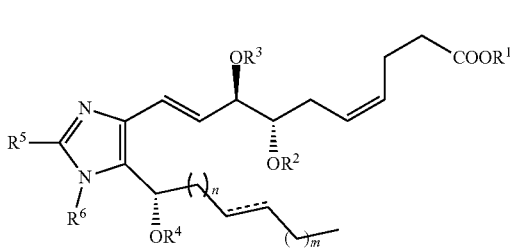

wherein $R^1$, $R^2$, $R^3$, $R^4$, $R^5$, $R^6$ and ⌇ are as defined in claim 1, and n and m are independently an integer from 0 to 7,
or an enantiomer, isomer, salt or solvate thereof.

3. The compound of claim 1, wherein $R^7$ is pentyl, propyl, octyl or benzyl.

4. The compound of claim 1, wherein $R^1$ is H, methyl, ethyl or propyl.

5. The compound of claim 1, wherein $R^1$ is H or methyl.

6. The compound of claim 1, wherein $R^2$, $R^3$ and $R^4$ are independently selected from the group consisting of H, methyl, ethyl, and propyl.

7. The compound of claim 1, wherein $R^2$ and $R^3$ are joined to form, together with the atom therebetween, an acetal group.

8. The compound of claim 1, wherein $R^2$, $R^3$ and $R^4$ are each H.

9. The compound of claim 1, wherein $R^5$ and $R^6$ are each H, methyl or ethyl.

10. The compound of claim 1, wherein $R^5$ and $R^6$ are each methyl.

11. The compound of claim 1 having the structure of Formula (I-2):

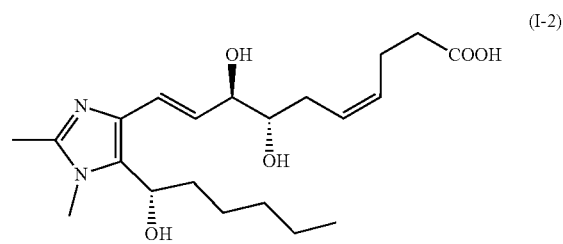 [SMILES: CCCCC[C@H](O)c1c(/C=C/[C@@H](O)[C@@H](O)C/C=C\CCC(=O)O)nc(C)n1C]

or an enantiomer, isomer, salt or solvate thereof.

12. The compound of claim 1 having the structure of Formula (I-1):

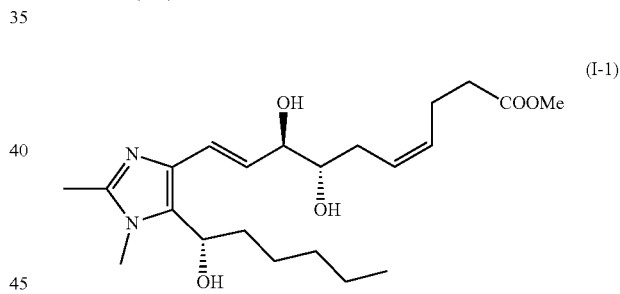

or an enantiomer, isomer, salt or solvate thereof.

13. The compound of claim 1 having the structure of Formula (IB)

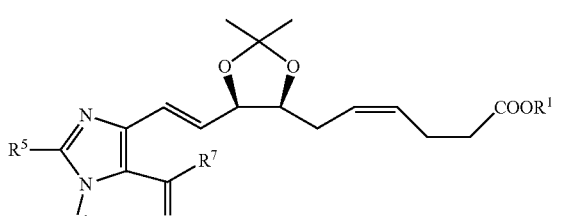

or an enantiomer, isomer, salt or solvate thereof.

14. The compound of claim 1 having the structure of Formula (IC)

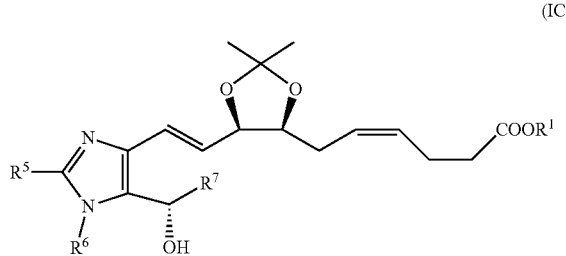

(IC)

or an enantiomer, isomer, salt or solvate thereof.

15. A pharmaceutical composition comprising a compound as defined in claim 1, or an enantiomer, isomer, salt or solvate thereof, and a pharmaceutically acceptable excipient, diluent or carrier.

16. A pharmaceutical composition comprising a compound as defined in claim 11, or an enantiomer, isomer, salt or solvate thereof, and a pharmaceutically acceptable excipient, diluent or carrier.

17. A pharmaceutical composition comprising a compound as defined in claim 12, or an enantiomer, isomer, salt or solvate thereof, and a pharmaceutically acceptable excipient, diluent or carrier.

18. A pharmaceutical composition comprising a compound as defined in claim 13, or an enantiomer, isomer, salt or solvate thereof, and a pharmaceutically acceptable excipient, diluent or carrier.

19. A pharmaceutical composition comprising a compound as defined in claim 14, or an enantiomer, isomer, salt or solvate thereof, and a pharmaceutically acceptable excipient, diluent or carrier.

20. A method for treating an inflammatory disease or disorder, comprising administering an effective amount of a compound as defined in claim 1 in a subject in need thereof.

21. The method of claim 20, wherein the inflammatory disease or disorder is selected from arthritis, osteoarthritis, inflammatory bowel disease or disorder, and skin inflammatory disease and disorder.

22. A method for inhibiting monocytes/macrophages differentiation, comprising administering an effective amount of a compound as defined in claim 1 in a subject in need thereof.

23. A method for inhibiting osteoclasts recruitment, comprising administering an effective amount of a compound as defined in claim 1 in a subject in need thereof.

24. A method for inhibiting MMP-13 production, comprising administering an effective amount of a compound as defined in claim 1 in a subject in need thereof.

25. A method for inhibiting ultraviolet-induced hyaluronic acid degradation, comprising administering an effective amount of a compound as defined in claim 1 in a subject in need thereof.

26. A method for inhibiting COX-2 expression, comprising administering an effective amount of a compound as defined in claim 1 in a subject in need thereof.

* * * * *